United States Patent [19]

Jacot et al.

[11] Patent Number: 5,219,400
[45] Date of Patent: Jun. 15, 1993

[54] NONINVASIVE METHOD FOR QUANTITATION OF OXYHEMOGLOBIN SATURATION BY NEAR-INFRARED REFLECTANCE SPECTROPHOTOMETRY

[75] Inventors: Jorge L. Jacot, Bethesda; John T. O'Neill, Damascus; Lou Reinisch, Clarksburg, all of Md.

[73] Assignee: The United States of America as represented by the Secretary of the Army, Washington, D.C.

[21] Appl. No.: 713,212

[22] Filed: Jun. 11, 1991

[51] Int. Cl.$^5$ .................................................. A61B 5/00
[52] U.S. Cl. ................................... 128/633; 128/664; 356/40; 356/41
[58] Field of Search .................. 128/633, 664–666; 356/40, 41

[56] References Cited

U.S. PATENT DOCUMENTS

| | | | |
|---|---|---|---|
| 4,305,398 | 12/1981 | Sawa | 128/633 |
| 4,485,820 | 12/1984 | Flower | 128/634 |
| 4,702,576 | 10/1987 | Magnante | 128/633 |
| 4,877,322 | 10/1989 | Hill | 128/633 |
| 5,070,874 | 12/1991 | Barnes et al. | 128/633 |

*Primary Examiner*—Lee S. Cohen
*Assistant Examiner*—Brian L. Casler
*Attorney, Agent, or Firm*—Werten F. W. Bellamy; Anthony T. Lane

[57] ABSTRACT

The degree of hemoglobin oxygenation in the blood vessels of the retina is determined under conditions of dark-adaptation and light-adaptation by directing a beam of near-infrared light having a range of wavelengths from 700 to 100 nanometers at a blood vessel in the retina, measuring the intensity of the backscattered light from the blood vessel in the range from 700 to 800 nanometers at regularly spaced intervals of wavelength, such as 2 nanometers, and determining the degree of hemoglobin oxygenation by reference to a correlation between hemoglobin oxygen and light absorbance in the near-infrared spectral range.

6 Claims, 2 Drawing Sheets

NONINVASIVE METHOD FOR QUANTITATION OF OXYHEMOGLOBIN SATURATION BY NEAR-INFRARED REFLECTANCE SPECTROPHOTOMETRY

GOVERNMENT INTEREST STATEMENT

The invention described herein may be manufactured, licensed and used by or for governmental purposes without the payment of any royalties thereon.

BACKGROUND OF THE INVENTION

1. Field of the Invention

This invention relates to apparatus and a noninvasive method for determining the oxygen-saturation of hemoglobin in the blood vessels of the fundus of the eye (human or animal). Specifically, it relates to the determination of the degree of hemoglobin oxygenation in the vasculature of the retina while the eye is dark (scoptic vision) or light-adapted (photopic vision). This technique can reveal subtle alternations in visual function which are not discernible with method currently available.

2. Description of the Prior Art

Optical methods for determining the degree of hemoglobin oxygenation, or oxygen saturation, in the blood vessels in the human eye are know to the art. Such methods are employed to diagnose early pathogenic states in the eye.

U.S. Pat. No. 4,305,398 discloses an oximeter for measuring the oxygen saturation of the blood in the fundus of the human eye using four different wavelengths. The reflected light outputs are compared at these wavelengths and the degree of oxygen saturation is calculated by suitable arithmetic operations.

U.S. Pat. No. 4,253,744 relates to an optical system for the measurement of pulse waves in the artery of the eye fundus or oxygen saturation therein. Light for illuminating the eye fundus is converged on the cornea and enters through pupil. Light reflected at the surface of the cornea is converged and blocked at its converging position while the light reflected from the eye fundus is allowed to pass by the light blocking member to reach a photocell.

U.S. Pat. No. 4,848,897 discloses an ophthalmic diagnosis apparatus having an optical spatial frequency filter and a double diffraction optical system generating two images of the eye fundus, and a detecting aperture for detecting movement of laser speckles.

U.S. Pat. No. 4,854,693 discloses an ophthalmic disease detection apparatus using laser beam and slit light to illuminate the eye. Protein particles at a specific spot in the eye are detected by the light scattering they produce.

U.S. Pat. No. 4,877,322 relates to an apparatus for measuring relative oxygen saturation of the choroidal blood of the fundus. Red and infrared light beams are directed into the eye, and the reflected light beam is split into red and infrared components and their respective intensity is measured. The resulting values are compared with the intensity of the incident non-reflected red and infrared light to determine the ratio of oxyhemoglobin to reduced hemoglobin.

U.S. Pat. No. 4,485,820 discloses an oximeter for continuously monitoring hemoglobin saturation in a premature infant's eye fundus by illuminating the eye with at least two frequencies of light. The light scattered by the fundus is collected and its intensity if measured. Blood hemoglobin is calculated from the intensity of the scattered light by known methods.

U.S. Pat. No. 4,394,074 provides optical apparatus for photographing the convex surface of the iris of the eye for optimum depth of field and resolution.

U.S. Pat. No. 4,854,699 provides a noninvasive backscatter oximeter utilizing two wavelengths in the visible range and two wavelengths in the near-infrared range.

U.S. Pat. No. 4,948,248 relates to an oximeter for determining the oxygen saturation of blood.

U.S. Pat. No. 4,908,762 employs near-infrared light transmission spectrophotometry for measuring oxygenation in brain issue and organs.

U.S. Pat. No. 4,850,365 employs near infrared light for measuring body fat content.

None of the known methods for determining hemoglobin oxygenation in the blood vessels of the eye fundus can investigate the physiology of the eye while dark-adapted, a state in which the metabolic level of the retina is higher than during the light-adapted state. Light and dark induced alternations in oxygen consumption can be investigated by the technique of this invention. Such subtle alternations are a regulatory phenomenon and an important pathogenetic component of many retinal vascular diseases which comprise the leading causes of blindness. The technique of this invention can be used for clinical intervention and early diagnosis of retinal vascular diseases.

SUMMARY OF THE INVENTION

Investigations of retinal metabolism during dark-adaptation offer a sensitive, noninvasive method for the early assessment of alternations in visual function. The object of this invention therefore is to provide a method and apparatus for determining the degree of oxygenation of hemoglobin in the vasculature of the retina while the eye is dark-adapted and/or light-adapted b directing a beam of light in the near-infrared spectral range through the pupil into the eye, focussing it upon the arterial system, e. g. on an artery, or the venous system, e. g. on a vein in the retina, measuring the intensity of the backscattered light from these blood vessels at discrete intervals of wavelength in the near-infrared spectral range, and determining the degree of hemoglobin oxygenation by reference to a correlation derived from in vitro and an vivo validation tests between the spectral characteristics of backscattered light and the degree of hemoglobin oxygenation.

By employing near infrared light via spot illumination in the broad range of wavelength of 700 to 1000 nanometers, the method of this invention assures that the eye is dark-adapted. Under conditions of dark-adaptation, the metabolic rate of the retina is higher than under conditions of light adaptation.

DESCRIPTION OF PREFERRED EMBODIMENT OF THE INVENTION

Figure 1:
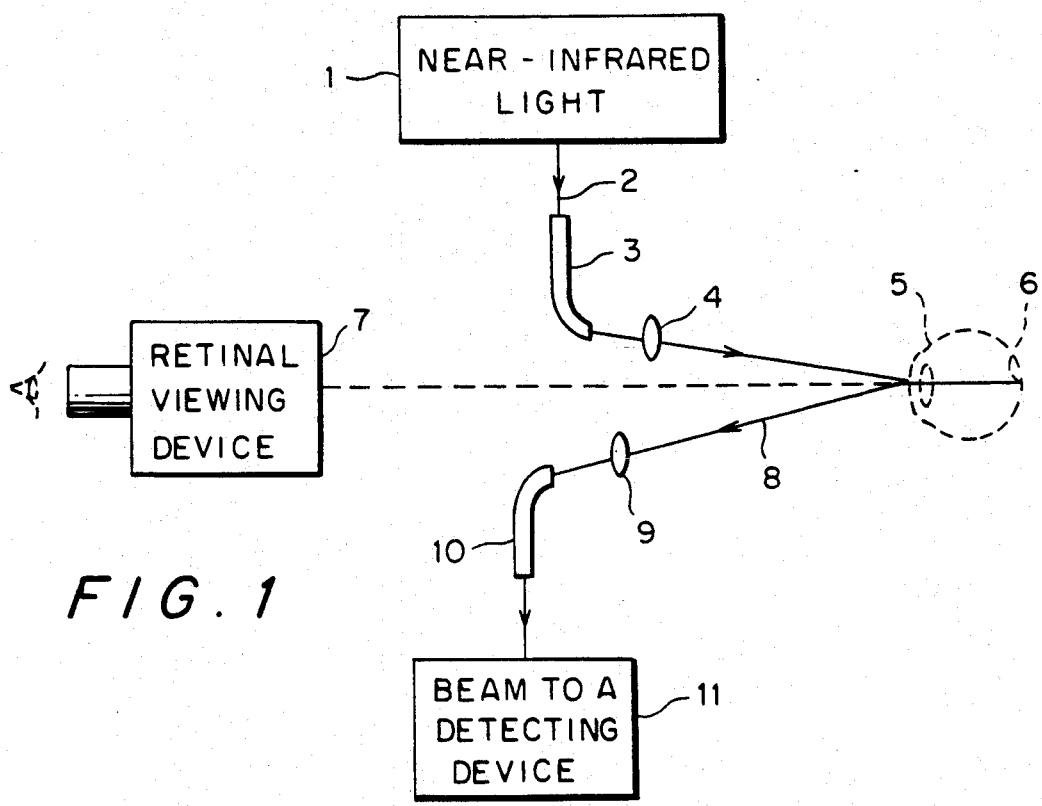
FIG. 1 shows a schematic diagram of the apparatus of the invention.

As shown in FIG. 1, there is shown a source 1 of near-infrared light in the broad spectral range of 700-1000 nanometers. This light source may be a halogen lamp or xenon arc lamp or an arc lamp emitting a beam whose visible portion is reflected by a cold mirror and whose near-infrared and infrared passes through the mirror. A heat absorbing filter then absorbs the infrared portion of the beam above 3 microns, allowing near-infrared radiation between 700 to 1000 nanometers to pass through.

The near-infrared beam thus generated, 2, is directed into an optic fiber 3 and conveyed to a lens 4 and transmitted into an eye 5 through the pupil, and focussed upon a blood vessel in the retina 6 or near the optic nerve head, which is devoid of photoreceptors. A retinal viewing device 7, such as a fundus camera or similar optical device, is used by the investigator to position the beam on the arterial system, e. g. on an artery, and/or on the venous system, e. g. on a vein, in the subject's retina under attenuated mild irradiation in the visible spectral range. Under near-infrared irradiation in the visible spectral range. Under near-infrared illumination, the light backscattered from the blood vessels along a beam 8 is collected by a lens 9 and enters a second fiber-optic bundle 10 conveying the beam to a detecting device 11.

This detecting device may be amonochromator coupled to a photomultiplier bike capable of measuring the intensity of the backscattered light. The intensity of the backscattered light is measured at predetermined intervals of wavelengths ranging from about 0.5 to about 3 nanometers, in the narrow range rom 700 to 800 nanometers. Intervals of about 2 nanometers are preferred.

An alternative means of detecting the intensity of the backscattered light from a blood vessel in the retina from 700 to 800 nanometers is an array of photodiodes onto which is projected the entire spectrum from 700 to 800 nanometers by a suitable device, each diode being sensitive to light over a small increment of wavelength.

Figure 2:
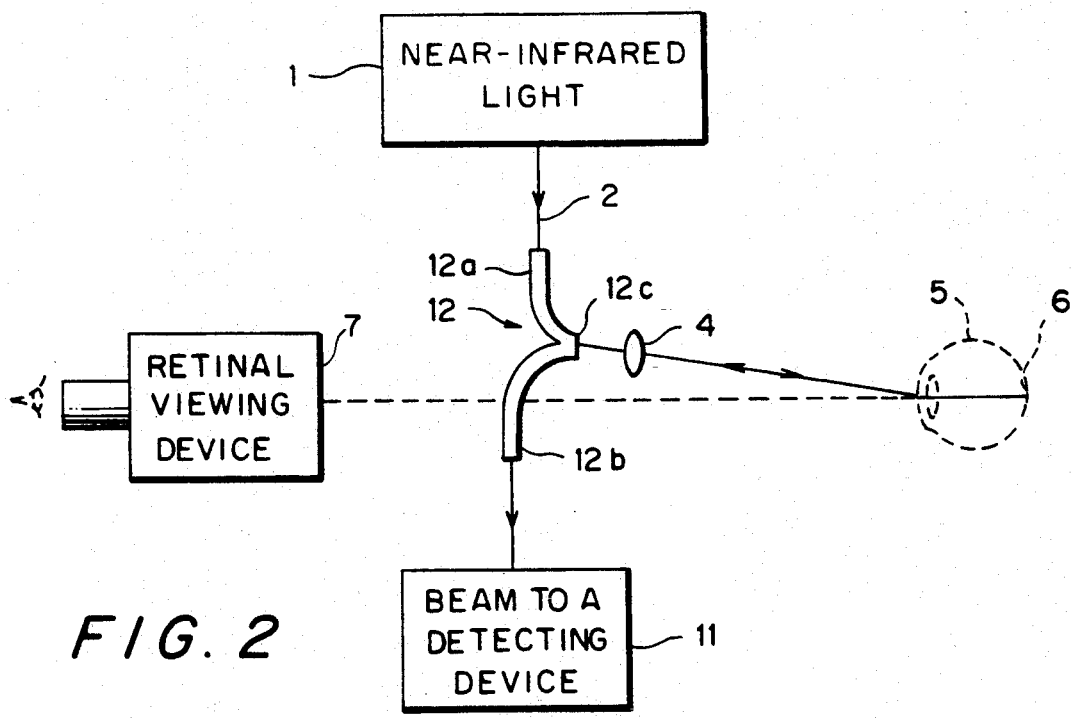
FIG. 2 shows an alternative embodiment of the apparatus.

An alternative embodiment of the invention is illustrated by FIG. 2. The fiber-optic bundles 3 and 10 of the first embodiment here are combined into a single, bifurcated fiber optics bundle 12 having two free ends 12a and 12b and one common end 12c, in which the beam 2 of near infrared light coming from the source of light 1 enters one free end of the bundle 12a and exits from the common end 12c of the bundle, and backscattered light from a blood vessel in the retina enters the common end 12c of the bundle via a different bundle track and exits from the other free end 12b of the bundle to the detecting means 11.

Outputs of the light detecting device are obtained while the apparatus is focused on the venous system after having been focused on the arterial system in the retina. The output from the arterial system, which contains fully oxygenated hemoglobin, establishes a baseline for comparison with the output from the venous system. Another required measurement is hematocrit, obtained by blood sample from the subject with a fingerprick.

Figure 3:
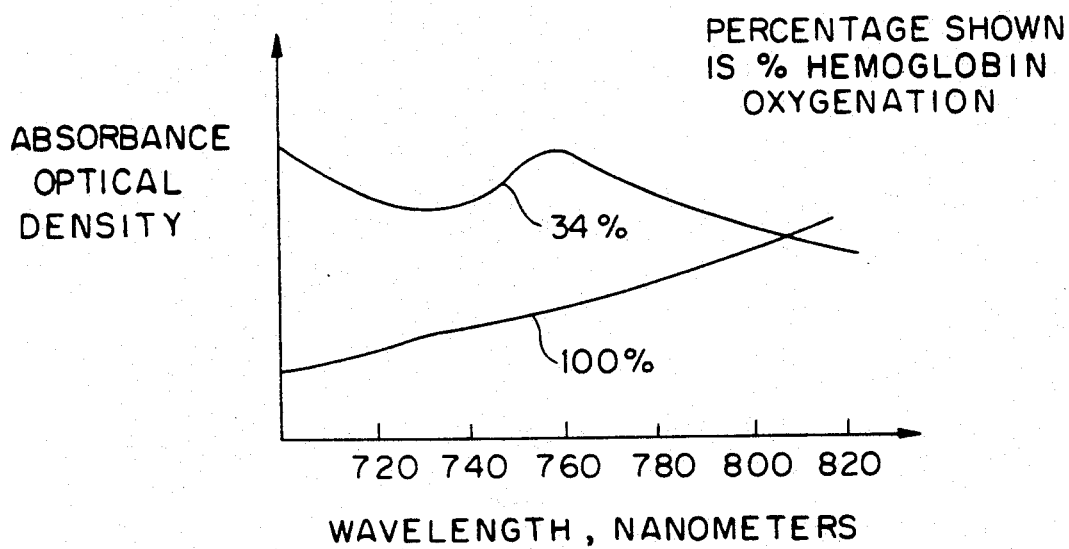
FIG. 3 shows plots of absorbance as a function of wavelength for fully oxygenated blood, and for blood having 34% hemoglobin oxygenation.

The outputs of the light detecting device are digitized and eventually expressed in terms of absorbance. FIG. 3 is an example showing absorbance in units of optical density as a function of wavelength for fully oxygenated blood and for blood having 34% hemoglobin oxygenation.

A correlation between the degree of hemoglobin oxygenation and absorbance in the near-infrared spectral range has been derived. In vitro tests of blood samples with known degree of hemoglobin oxygenation were infused into a glass capillary having an internal diameter of 1500 microns, transversing a container filled with saline solution which mimics the refractive index of the vitreous humor. A glass lens with a focal length similar to that of the a human mimics the optical properties of a human lens mimics the human lens. The background of the container simulates the specular and diffuse reflection from the retina. A beam of light approximately 200 microns in diameter, in the broad range of wavelength from 700 to 1000 nanometers, is directed onto the glass capillary tube, and the backscattered light from the blood filled capillary is detected over the narrow range from 700 to 800 nanometers at predetermined intervals of wavelength, by a light detecting device as described above.

A curve-fitting program called "CurveFit," by P. R. Befington, described in "Data Reduction and Error Analysis for the Physical Sciences," McGraw-Hill Inc., St. Louis, 1969, is used to express the spectral data as a Gaussiam distribution at regularly spaced intervals of wavelength in the spectral range from 730 to 796 nanometers. The height of the Gaussian-fitted absorption peak at almost 760 nanometer is correlated with the degree of hemoglobin oxygenation by linear regression analysis. The quantitation of the absorption spectra of backscattered light from hemoglobin in the near-infrared or infrared region is accomplished by expressing the measured spectral data as a Gaussian or Lorenzian distribution and utilizing a common least-squares method to optimize the fit. Automated curve fitting software such a PeakFit and table curve from Jandel Scientific Inc. or Graph Pad Inc. may be used. Any mathematical characterization of the absorption spectra may be applied when the measured spectral data are fitted a the sum of Gaussian or Lorenzian distributions. The contents of the above-mentioned reference are incorporated herein by reference.

In the determination of the degree of hemoglobin oxygenation in the vasculature of a subject's retina, the mathematical relationships derived from in vitro and in vivo tests are utilized to develop an algorithm which can calculate the degree of hemoglobin oxygenation from the absorbance measurements of hemoglobin spectral data taken from the vasculature of the subject's retina in the near infrared spectral range. These calculations are carried out by digital computer. The subject's hematocrit, determined from a blood sample from a fingerprick, also enters into these calculations.

Other modifications of this invention will be apparent to those skilled in the art, all falling within the scope of the invention as described herein and claimed in the following appended claims.

What is claimed is:

1. A noninvasive method of determining the degree of oxygenation of hemoglobin in the blood vessels of the retina comprising directing a beam of light in a broad range of wavelengths in the near-infrared spectral range into an eye through the pupil, focussed upon a blood vessel in the retina;

measuring the intensity of backscattered light from the blood vessel in a narrow range of wavelengths in the near-infrared spectral range; and determining the degree of oxygenation of hemoglobin in the blood vessel by reference to a correlation derived from validation tests between the intensity of the backscattered light from the blood vessel and the degree of oxygenation of hemoglobin in the blood vessel in the retina.

2. The method of claim 1 in which the broad range of wavelengths is from 700 to 1000 namometers.

3. The method of claim 1 in which the narrow range of wavelengths is from 700 to 800 nanometers.

4. The method of claim 1 in which the intensity of the backscattered light from the blood vessel is measured at predetermined intervals of wavelength from 0.5 to 3 namometers.

5. The method of claim 1 in which the intensity of the backscattered light from the blood vessel is measured at predetermined intervals of wavelength of about 2 namometers.

6. The method of claim 1 in which the correlation is derived from in vitro and in vivo measurements of the intensity of light scattered in the narrow range of wavelength by a glass capillary containing blood of known degree of hemoglobin oxygenation.

* * * * *